(12) United States Patent
Friedberger et al.

(10) Patent No.: US 9,557,259 B2
(45) Date of Patent: Jan. 31, 2017

(54) OPTICAL PARTICLE DETECTOR AND DETECTION METHOD

(75) Inventors: Alois Friedberger, Oberpframmern (DE); Ulrich Martin, Ottobrunn (DE); Leonhard Meixner, Munich (DE)

(73) Assignee: EADS Deutschland GmbH, Ottobrunn (DE)

( * ) Notice: Subject to any disclaimer, the term of this patent is extended or adjusted under 35 U.S.C. 154(b) by 1575 days.

(21) Appl. No.: 13/056,374

(22) PCT Filed: Jul. 22, 2009

(86) PCT No.: PCT/EP2009/059452
§ 371 (c)(1),
(2), (4) Date: May 20, 2011

(87) PCT Pub. No.: WO2010/012644
PCT Pub. Date: Feb. 4, 2010

(65) Prior Publication Data
US 2011/0311996 A1     Dec. 22, 2011

(30) Foreign Application Priority Data

Jul. 31, 2008 (DE) .................. 10 2008 035 770

(51) Int. Cl.
*G01N 15/14* (2006.01)
*B01D 67/00* (2006.01)
(Continued)

(52) U.S. Cl.
CPC ....... *G01N 15/1475* (2013.01); *B01D 67/0062* (2013.01); *B01D 71/021* (2013.01); *G01N 35/0098* (2013.01); *G01N 2001/2217* (2013.01)

(58) Field of Classification Search
CPC ............ G01N 15/1434; G01N 15/1475; G01N 35/0098; G01N 2001/2217; B01D 67/0062; B01D 71/021
(Continued)

(56) References Cited

U.S. PATENT DOCUMENTS 4,291,938 A    9/1981  Wagner
5,854,684 A   12/1998  Stabile et al.
(Continued)

FOREIGN PATENT DOCUMENTS

DE        693 25 652 T2   10/1999
DE   10 2006 053 540 B3    1/2008
(Continued)

OTHER PUBLICATIONS

Yang et al. Nature Materials, 2002, 1, p. 253-257.*
(Continued)

*Primary Examiner* — Gail R Gabel
*Assistant Examiner* — Pensee Do
(74) *Attorney, Agent, or Firm* — Global IP Counselors, LLP

(57) ABSTRACT

A particle detector apparatus for optically ascertaining a number of particles arranged on a surface of, for example, a particle filter. The particle detector apparatus includes a light source, an optical focusing device, a spatially resolving light detector and an evaluation device. The light source emits source light onto the surface. The optical focusing device focuses image light that is emitted from the surface in response to the source light onto the spatially resolving light detector. The spatially resolving light detector includes light sensors that measure brightness values based on the image light, such that the light detector produces image data based
(Continued)

on the brightness values delivered by the light sensors. The evaluation device then ascertains the number of particles based on the image data.

26 Claims, 6 Drawing Sheets

(51) Int. Cl.
 *B01D 71/02* (2006.01)
 *G01N 35/00* (2006.01)
 *G01N 1/22* (2006.01)
(58) Field of Classification Search
 USPC .............................................. 422/50; 436/518
 See application file for complete search history.

(56) References Cited

U.S. PATENT DOCUMENTS

| | | | |
|---|---|---|---|
| 7,122,384 B2* | 10/2006 | Prober et al. | 436/524 |
| 2002/0014443 A1* | 2/2002 | Hansen et al. | 209/213 |
| 2002/0021491 A1 | 2/2002 | Engelhardt | |
| 2002/0062702 A1 | 5/2002 | Bradley | |
| 2003/0058530 A1 | 3/2003 | Kawano | |
| 2004/0125441 A1 | 7/2004 | Wang et al. | |
| 2005/0112784 A1* | 5/2005 | Yguerabide et al. | 436/518 |
| 2005/0231715 A1 | 10/2005 | Horigome et al. | |
| 2006/0134397 A1* | 6/2006 | Smith | 428/304.4 |
| 2006/0257854 A1* | 11/2006 | McDevitt et al. | 435/5 |
| 2008/0273205 A1* | 11/2008 | Lee et al. | 356/440 |
| 2009/0047297 A1 | 2/2009 | Kim et al. | |
| 2009/0131858 A1* | 5/2009 | Fissell | B01D 61/145 604/57 |
| 2010/0315628 A1 | 12/2010 | Mertsching et al. | |

FOREIGN PATENT DOCUMENTS

| | | |
|---|---|---|
| EP | 0-949-200 A1 | 10/1999 |
| EP | 1-168-031 A2 | 1/2002 |
| EP | 1-657-228 A1 | 5/2006 |
| GB | 2-221-404 A | 2/1990 |
| GB | 2-416-263 A | 1/2006 |
| JP | 02-006729 A | 1/1990 |
| JP | 07-167852 A | 7/1995 |
| WO | WO-93/21511 A1 | 10/1993 |
| WO | WO-98/53300 A2 | 5/1998 |
| WO | WO-2005/090983 A2 | 9/2005 |
| WO | WO-2006/021410 A1 | 3/2006 |

OTHER PUBLICATIONS

German Office Action issued on Feb. 9, 2011 corresponding German Application No. DE-10,2008,035,770.7-52.
International Search Report of corresponding International Application No. PCT/EP2009/059452, dated May 18, 2010.

* cited by examiner

OPTICAL PARTICLE DETECTOR AND DETECTION METHOD

CROSS-REFERENCE TO RELATED APPLICATIONS

This U.S. National stage application claims priority under 35 U.S.C. §119(a) to German Patent Application No. 10 2008 035 770.7, filed in Germany on Jul. 31, 2008, the entire contents of which are hereby incorporated herein by reference.

BACKGROUND

Field of the Invention

The present invention relates to a particle detector apparatus for optically ascertaining a number of particles arranged on a surface, in particular of a particle filter. The invention furthermore relates to a particle detection method for optically ascertaining a number of particles arranged on a surface, in particular of a particle filter.

Background Information

The particle detector apparatus is intended to be used to quantify the loading of fluids with certain particles, in particular microbiological particles, for example with bacteria. In particular, to this end the fluid to be analyzed is intended to be pressed through a particle filter in which the particles become mechanically fixed. Depending on the type of particles to be detected, marking substances are intended to be used, the effect of which is that the particles to be analyzed can be distinguished optically from the particle filter and from other particles.

In the prior art, it is known for example to treat bacteria with fluorescent substances, which emit light in certain colors according to the incident light and can therefore easily be distinguished from the surroundings. In the known particle detection methods, the total intensity of the emitted light is generally measured in order to determine the particle density. Other particle detection methods use complicated and expensive electron microscopes for determining the particle number.

Such detection methods require a large number of user operations for positioning the detectors and the particle filters. Furthermore, calibration of the measurement results is virtually impossible. There are no automated instruments which can carry out such a particle detection method. If a photomultiplier is used, then a cumulative signal is measured by which the number of particles present can only conditionally be deduced.

SUMMARY

It is an object of the invention to provide a particle detector apparatus of the type mentioned in the introduction, which is easier to handle than known particle detector apparatuses and the accuracy of which is increased. It is also an object to refine a particle detection method of the type mentioned in the introduction so that its accuracy is increased.

In order to achieve this object, a particle detector apparatus of the type mentioned in the introduction is proposed, which is provided with a spatially resolving light detector, a light source, an optical focusing device and an evaluation device, and in which the spatially resolving light detector has light sensors which measure brightness values, the light detector being designed to produce digital image data from the brightness values delivered by the light sensors.

The co-ordinated claim relates to an advantageous detection method which can be carried out therewith, and preferred uses of the particle detection apparatus.

The dependent claims relate to advantageous configurations of the invention.

The particle detector apparatus according to the invention has the advantage that individual particles can be imaged by a spatially resolving light detector. With the aid of the digital image data, it is therefore possible to count the actual number of particles. Effects due to the size and brightness of the particles are neutralized.

The light sensors may be configured as an integrated circuit—in particular on one or more chips—and/or as CCDs, as a CMOS or as a diode array. These types of light sensors can be read out quickly but nevertheless deliver a good brightness resolution.

The light source may have an LED, which provides an economical and reliable light source.

The light source may advantageously have a laser. In this way, with monochromatic light, it is possible to excite an accurately defined reaction of the particles to be analyzed.

The light source or the focusing device advantageously has an optical filter. With such a filter, it is readily possible to attenuate effects of ambient light or of reflections at the filter.

In an advantageous configuration, a particle detector apparatus is provided for changing the optical filter. In this way, it is possible to observe the particles to be analyzed in different color spaces and/or with light of different polarization and wavelength, and thus further improve the accuracy of the detection.

The light source may advantageously be arranged in a mobile fashion. In this way, by different exposure of the particles, it is possible to obtain information about their topology. Subregions of the surface, on which the particles to be detected are arranged, may also be scanned in succession with a beam of the light source, so as to obtain a scan of the surface.

A plurality of light sensor units may be arranged in a grid, a beam splitter being provided for distributing the image of the surface onto the light sensor units and the evaluation device being designed to compile an overall image from the image data of the light sensor units. This firstly has the advantage that larger surfaces can be observed. With an increasing size, the light sensor units used are generally more complicated, more expensive to handle and less readily available. The possibility of arranging a plurality of smaller light sensor units in a grid, and subdividing the image to be recorded into smaller sections, opens up the possibility of using comparatively economical components with increased accuracy of the imaging. Furthermore, pre-processing of the data may be carried out for each sensor unit, in order to increase the processing speeds of the evaluation unit.

The particle detector apparatus may have a positioning device, on which at least one of the light sensor units is fastened for positioning relative to the surface. In this way, it is possible to further reduce the costs for the light sensor units. Thus, a large area can be scanned with a relatively small light sensor unit which is easy to handle.

When using a CCD row as a light sensor, a deflection device may be provided which projects different sections of the surface onto the CCD row. This permits a very simple but nevertheless reliable set-up.

In the advantageous particle detection method for optically ascertaining a number of particles arranged on a surface of a particle filter, advantageously by means of a particle detector apparatus according to the invention, the surface having the particles is illuminated with the light source and an image of the surface is recorded by the detector device. The image data are transmitted to the evaluation device. Finally, the particles are counted and evaluated by the evaluation device with the aid of the image data.

The particle detection method according to the invention makes it possible to count the actual number of particles. This improves the accuracy of the measurement compared with measuring a cumulative signal, since the result is independent of the size of the individual particles and their possibly different ability to take up the marking substances.

Before counting the particles, a reference image of the surface without particles may be recorded. It is thereby possible for interfering effects, which result from the structure of the particle filter or for example from errors in the light sensors, to be cancelled out from the end result. With these particle detection methods, for example, the state of cleanliness on the particle filter can be checked.

Advantageously, a plurality of images of the surface are recorded and the position of the light source is modified between the recordings. In this way, the particles are illuminated from different directions and, for example, covered particles can be identified. Furthermore, it is thereby possible to obtain information about the size of the recorded particles.

A plurality of images of the surface may be recorded and the type and/or number of optical filters used may be modified between the recordings. If the particles emit only in a certain spectrum, then the contrast with respect to the surroundings of the particles can thus be increased.

In an advantageous configuration, in order to detect fluorescent particles, the surface is first exposed to a light pulse of the light source and an image of the surface with the particles is recorded after the light pulse has decayed. In the resulting image, the fluorescent particles can be identified with a greater contrast than during exposure to light.

The evaluation device advantageously evaluates the images together and calculates a particle number therefrom. The information of all recordings can thereby be used in order to increase the accuracy.

The particle detection apparatus is particularly suitable as a detection unit in an (analysis) apparatus and an (analysis) method for detecting particles in a particle-fluid mixture, which can respectively be operated and carried out fully automatically, are universally usable and can be implemented in a compact and simply constructed, preferably mobile system.

With a particularly preferred overall system as proposed here, rapid and fully automatic enrichment, extraction and detection of microorganisms (for example bacteria, protozoa, fungi, viruses) and biological particles (for example spores) is possible. The enrichment, extraction and detection may be carried out both from gases, in particular air, and from liquids. Besides the detection of biological materials, enrichment, extraction and detection of nonbiological or synthetic materials is also possible, in particular explosives, liquid explosives and drugs.

With the new technique used in this case, it is proposed in particular to use paramagnetic so-called beads in conjunction with a collection device, in particular an air sampler. The beads are coated with antibodies, which can in turn bind molecules or particles of biological or nonbiological origin. By using special enrichment techniques, extreme concentration and immobilization of the beads loaded in this way is achieved. Furthermore, fully automatic extraction and detection of the bound molecules or particles following the concentration is proposed. The high degree of concentration allows highly sensitive detection of the analytes. For automated detection, the particle detection apparatus according to the invention is particularly suitable.

In particular, the following advantages are achieved by such an overall system or its advantageous configurations:
rapid and sensitive detection of microorganisms and other hazardous substances (for example biological toxins) as well as explosives from a gas phase, in particular air;
rapid detection of microorganisms and other hazardous substances from liquids and liquid foodstuffs of all types;
combination and automation of the three fields of enrichment, extraction and detection in an integral, compact and mobile system and/or
rapid detection of pathogens from bodily fluids, in particular blood, saliva, tear fluid and urine (medical diagnosis).

The particle detection apparatus is particularly suitable for detecting the number of particles in a particle filter. To this end, a mechanical particle filter is preferably provided with a membrane which has a multiplicity of pores. Such particle filters are used to filter particles, for example bacteria, from a fluid. The particles filtered out can be analyzed in order to establish the loading of the fluid with certain particles.

The particle detection apparatus is preferably usable universally for measuring particles in different fluid-particle mixtures. It is furthermore advantageous that the particle filter can be changed, transported and used repeatedly in an automated system. The use of an in particular mechanical particle filter, which has high mechanical and chemical stability, is therefore preferred. For this reason, in a particularly preferred configuration of the invention, a particle filter is provided in which at least one subregion of a surface of the membrane, which is accessible for a medium to be filtered, is made of carbon material having a diamond structure and/or coated therewith.

Such a particle filter has the advantage that the carbon material with a diamond structure is almost entirely inert chemically. Simple cleaning, that is to say removal of the particles enriched by the filter, is therefore easy to carry out since the particles substantially do not form firm bonds with the membrane. Furthermore, a carbon material with a diamond structure is mechanically very stable, so that a high pressure difference between the two sides of the membrane can be employed when using the filter. This increases the flow rate through the filter.

The membrane may be made entirely of carbon material. Since the carbon material is transparent owing to its diamond structure, a membrane constructed in this way makes it readily possible to identify residual contamination after cleaning or structural defects in the membrane simply by shining light through the membrane.

The membrane may be made entirely of diamond.

The membrane is preferably supported by a carrier, on which it is fastened. This further increases the load-bearing capacity of the particle filter.

The carrier may be formed from a material which can be structured by lithography methods. This makes it possible to use the frame material as a support during production of the membrane and subsequently remove it from the porous region of the membrane without causing damage.

In an advantageous configuration, the material of the carrier has a crystal structure which dictates the direction of an anisotropic etching process. In such a material, the shape of the carrier can be determined reliably.

The carrier may be formed from silicon. Silicon has the advantage that it is available inexpensively, can be processed by lithography in industrially known methods and is mechanically stable.

Advantageously, the silicon has a (110) orientation. Owing to this orientation, carrier side walls which are almost entirely plane and perpendicular to the surface of the membrane are obtained during etching after the lithography.

BRIEF DESCRIPTION OF THE DRAWINGS

Details and further advantages of the particle detector apparatus according to the invention and the particle detection method according to the invention may be found in the following description of preferred exemplary embodiments. In the drawings which represent the exemplary embodiments merely schematically, the following are illustrated in detail.

DETAILED DESCRIPTION OF EMBODIMENTS

Figure 1:
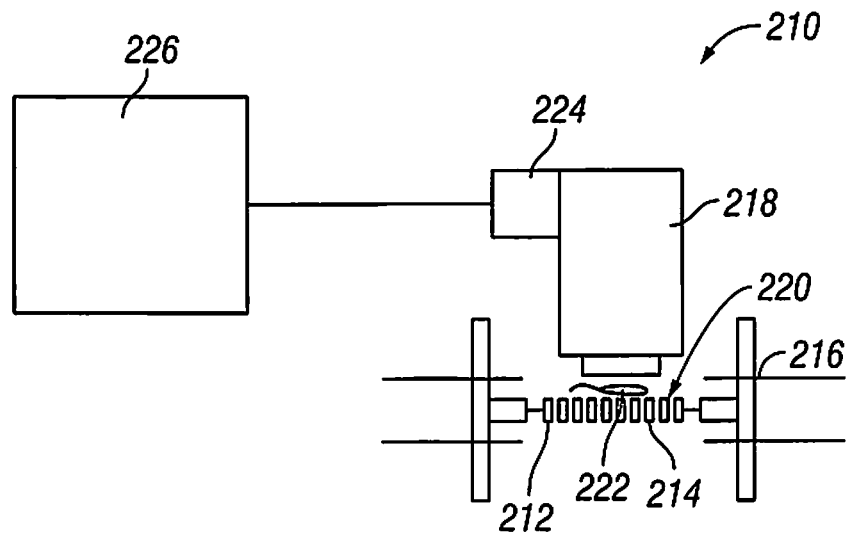
FIG. 1 illustrates an example of an overall structure of a particle detection apparatus for measuring a particle number.

A particle detector apparatus 210 shown in FIG. 1 for measuring a particle number has a microfilter or particle filter 214 as a filter element 212. The particle filter 214 has pores having a diameter with which particles 222 to be counted are retained on the particle filter 214. In order to fix and/or position the particle filter 214, a holding apparatus 216 is provided.

A two-dimensionally spatially resolving light detector 218 is arranged in relation to the particle filter 214 so that the light detector 218 can acquire a surface 220 of the particle filter 214 with the particles 222 arranged thereon. The light detector 218 converts the acquired image of the surface 220 into digital image data and transmits it via a communication device 224 to an evaluation device 226.

Figure 2:
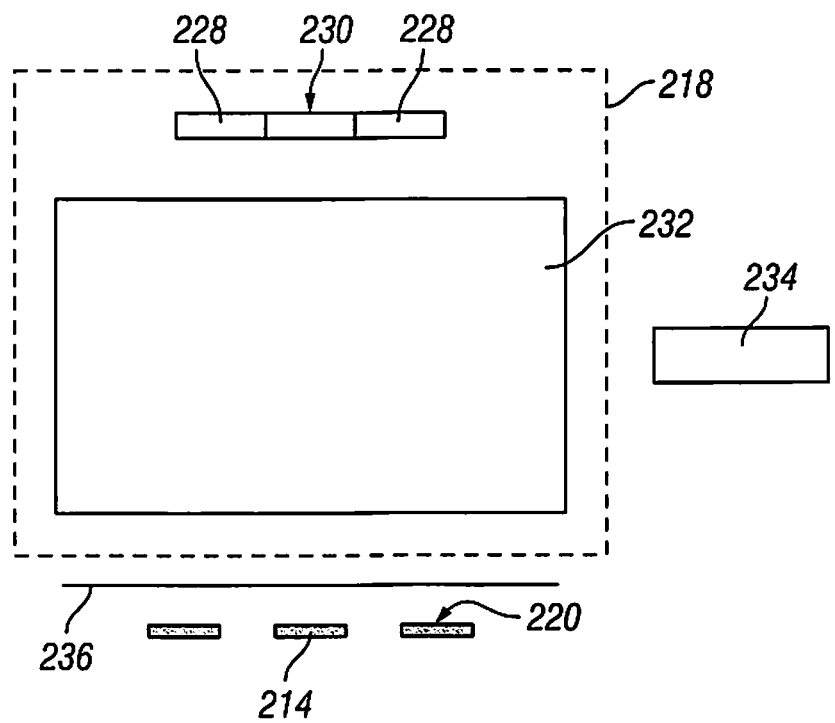
FIG. 2 is a detailed view of the structure in FIG. 1.

FIG. 2 represents an exemplary embodiment of the light detector 218. The light detector 218 which is shown in FIG. 2 has light sensors 228, here in the form of a CCD array 230. In order to form the image of the surface 220 of the particle filter 214, an optical focusing device 232 is provided. In order to illuminate the surface 220, the particle detector apparatus 210 has a light source 234. A glass cover 236 separates the particle filter 214 from the light detector 218.

Figure 3:
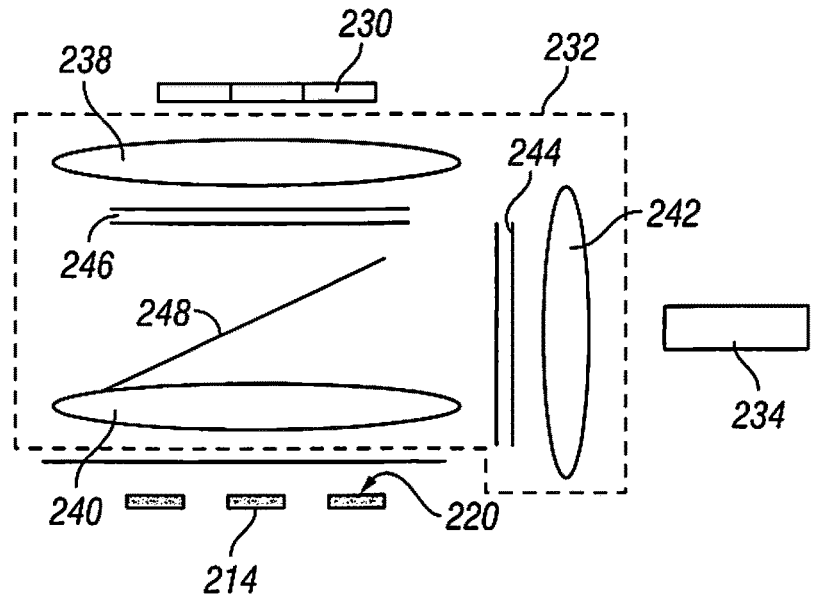
FIG. 3 is a detailed view with an example of an optical focusing device.

FIG. 3 represents an exemplary embodiment of the focusing device 232. The optical focusing device 232 has, as shown in FIG. 3, a first lens system 238, a second lens system 240 and a third lens system 242. The lens systems 238, 240, 242 respectively have at least one lens or an arrangement of a plurality of lenses.

In order to be able to illuminate the surface 220 of the particle filter 214, light from the light source 234 is passed through the third lens system 242 and through a first optical filter 244. The light subsequently strikes a beam splitter 248, which deflects a fraction of the light in the direction of the surface 220, so that the surface 220 is illuminated.

The light reflected or fluoresced by the surface 220 and/or the particles 222 travels through the second lens system 240 and the beam splitter 248 to a second optical filter 246, and is focused by the first lens system 238 onto the CCD array 230.

The lens systems 238, 240, 242 may be arranged in a mobile fashion, in order to be able to carry out adjustments.

The optical filters 244, 246 can be changed in an automated fashion. For example, color filters and/or polarization filters can be provided in a changeable fashion. In this way, automated recordings can be made in different color spectra or with different polarizations.

The light source 234 may also be designed for direct illumination of the surface at different positions 234a, 234b, 234c from different angles. In one embodiment, to this end the light source 234 is mounted positionably. In another embodiment, a plurality of light sources are provided, for example one light source per position, as represented at 234a, 234b, 234c.

Particles 222, for example molecules, macromolecules or microorganisms on or in the vicinity of a surface 220 are intended to be detected by the particle detector apparatus 210. In particular, the sample to be analyzed may be pumped through a filter element 212, in particular a micromechanical particle filter 214. The particles 222 to be detected are located on the surface 220. They may be marked by dyes, in particular fluorescent dyes. In particular, bacteria, viruses or toxins may be detected by fluorescence-marked antibodies.

After exposure of the surface 220 using the light source 234, the emitted light is not measured as a total intensity. Rather, an image of the surface 220 is made so that the light-emitting particles 222 can be counted by means of suitable software. In one embodiment of the particle detector apparatus 210, light sensors 228 are provided on a CCD chip with a CCD array 230.

In order to be able to count bacteria, owing to the typical size of bacteria, the lower limit of the optical resolution on the surface 220 should if possible be about 100 to 500 nm. To this end, for example, the image of the surface is magnified by means of a suitable optical focusing device 232. With a resolution of for example 5 μm on the CCD array 230, a magnification at least by a factor of ten is provided. In order to image a surface 220 of for example 5 mm×5 mm, a CCD area of at least about 5 cm×5 cm is then for example provided. With a correspondingly large CCD array 230, it is therefore possible to make a recording of the entire surface 220 directly.

Instead of a CCD array, it is also possible to use a CMOS, a diode array or an intensified CCD, in order to provide the light sensors 228. It is also possible to scan the surface linewise.

If the required CCD area exceeds the available area of a CCD chip, it is possible to arrange a plurality of smaller CCD chips in an array so as again to obtain an image of the entire surface 220. In a preferred exemplary embodiment, however, the CCD chips are not arranged edge to edge since the sensitive regions of the individual chips generally do not extend as far as their edges. Instead, a part of the surface 220 is projected onto each chip by means of a beam splitter 248 and further optical components. In this case, an overlap may occur. In order to obtain the entire image reliably, it is more advantageous to allow a certain overlap everywhere in order to compensate for inaccuracies, than to lose a part of the images owing to such inaccuracies. By means of suitable data processing, such an overlap is automatically removed in the evaluation unit 226 in order to avoid errors in the automatic counting of the particles 222.

In another advantageous embodiment of the particle detector apparatus 210, the light sensors 228 are configured as parts of a CCD row which scans the surface 220 line by line. The scan direction orthogonally to the CCD row may be achieved by imaging by means of a tilting mirror or by a precise displacement of the CCD row. An overall image may also be compiled from a plurality of recordings with a displaced CCD array 230. To this extent, the CCD row merely represents a special form of the CCD array 230.

Figure 4:
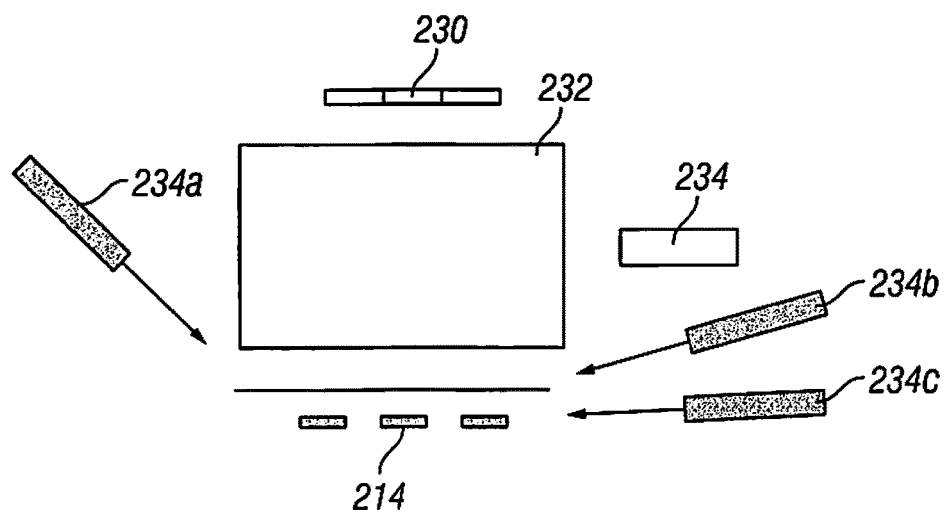
FIG. 4 is a view as in FIG. 2 with different arrangements of light sources.

FIG. 4 shows an exemplary embodiment of the particle detector apparatus 210, by means of which position- and time-resolved illumination is possible. This means that different images are recorded successively. The studied object does not change, but the type of illumination does, so that different images are obtained. These changes are also referred to as a synthetic optical aperture.

With suitable data processing, the resolution can thereby be improved significantly. The achievable improvement is commensurately greater when the images under different illumination differ more. It is advantageous that the particles 222 to be detected are not round, and that the dyes are distributed inhomogeneously in or on the particles 222, as for example fluorescent dyes in bacteria.

The method of position- and time-resolved illumination is also used in order to ascertain whether particles 222 have agglomerated.

To this end, it may be advantageous for the illumination to take place in a very flat fashion. Furthermore, a transparent particle filter 214 may itself be used as a light guide. With such transparent particle filters 214, the filtration and detection may also take place in the pores by means of antibody/antigen interaction or DNA hybridization. In particular, this is one possibility for the detection of small molecules such as toxins or viruses.

Another possibility for position- and time-resolved illumination consists in moving the light source 234, particularly in a plane perpendicular to the beam path. Besides the greater dynamic range in the detection, multiple illumination also gives additional information from the topography, which increases the information content of the recording by additional degrees of freedom.

In another advantageous exemplary embodiment of the particle detector apparatus 210, and of the particle detection method which can be carried out with it, reference images are made between different measurement cycles, i.e. without particles 222 on the particle filter 214, in order to ascertain whether individual light sensors 228 (CCD pixels) are defective. This can be compensated for by software, in order to avoid errors due to a pixel failure. A warning message may furthermore be generated, in order to avoid false measurements; optionally, response may be carried out by replacing the light sensors or the CCD apparatus.

LEDs or lasers may be used as the light source 234. Optical filters 244, 246 (edge and/or bandpass filters) make it possible to restrict the wavelengths. The optical filters 244, 246 may be changed automatically by a mechanical filter changing device, in order to carry out measurements with different wavelengths.

Additionally, direct optical recording may be carried out besides the fluorescence detection, in order to distinguish dust, dirt and other extraneous particles from the particles 222 to be detected. This may be combined with position- and time-resolved illumination.

A significant improvement of the signal-to-noise ratio is to be expected when the light of the light source 234 is pulsed. For example, the fluorescent light is not detected until the excitation pulse has decayed.

If the particle filter 214 is made of transparent material, then it may be illuminated from the other side so that the light follows a path through the particle filter 214. Such recordings may also be used without particles 222 in order to be able to identify structural defects in the particle filters 214 or insufficient cleaning. This information may be evaluated in such a way that a warning indication is given or the particle filter 214 is changed.

Exemplary embodiments of the particle filter 214 will be explained in more detail below with the aid of FIGS. 5 to 9.

Figure 5:
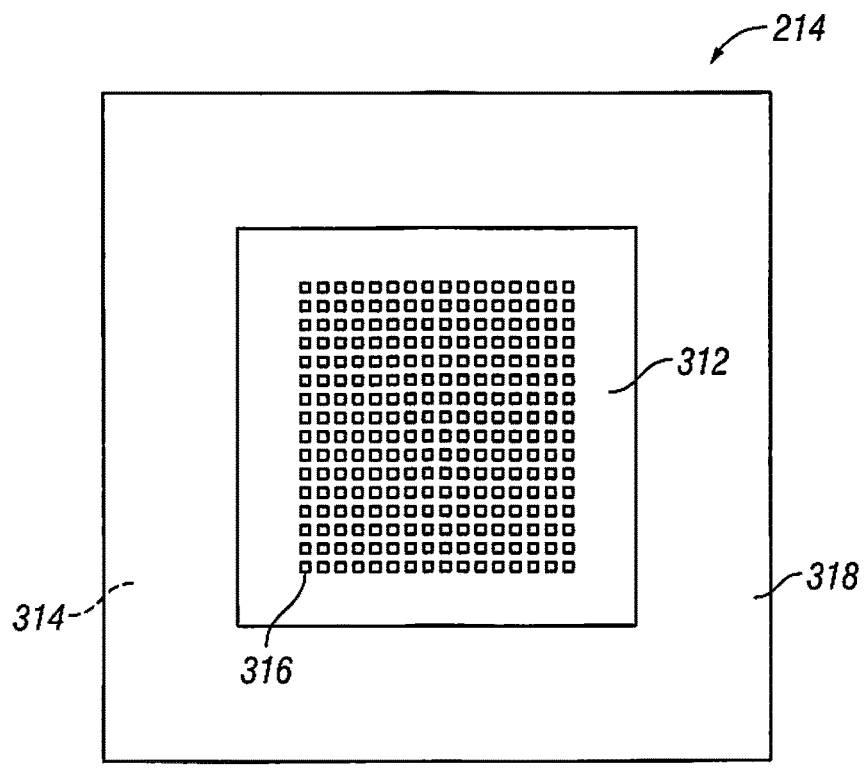
FIG. 5 is a plan view of an exemplary embodiment of a particle filter used in the particle detection apparatus of FIG. 1.
Figure 6:
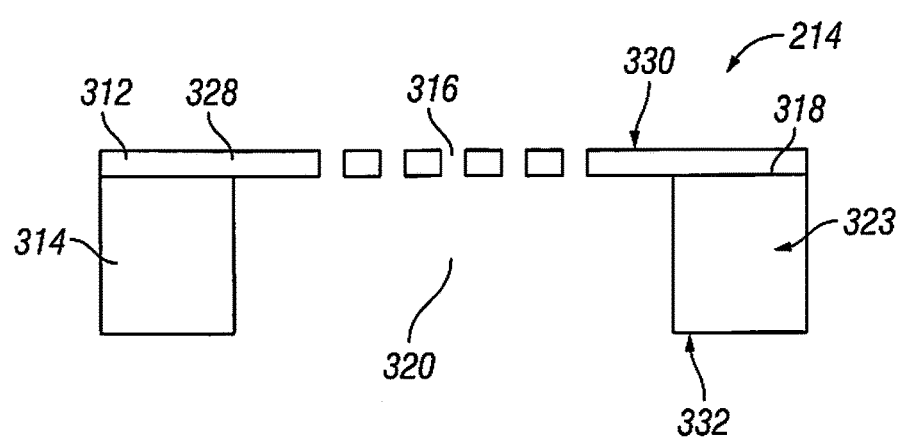
FIG. 6 is a cross section through the particle filter along the line II-II in FIG. 5.

The particle filter 214 shown in FIG. 5 and FIG. 6 has a membrane 312 and a carrier 314. Pores 316, which are arranged in a grid, are made in the membrane 312. The pores 316 have a round or square cross section.

The carrier 314 supports the membrane 312 in an edge region 318. A flow region 320 is provided in the region of the pores 316.

Figure 7:
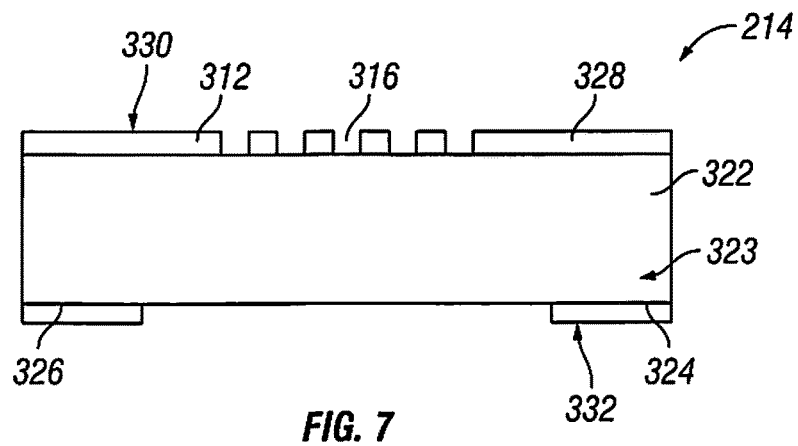
FIG. 7 is a cross section through the particle filter as in FIG. 6 during a production step for the particle filter.

As shown in FIG. 7, a silicon wafer 322 with a (110) crystal orientation is provided as the starting material for producing the particle filter 214.

The silicon is thermally oxidized, so that for example $SiO_2$ 324 with a thickness of about 500 nm is produced. The $SiO_2$ 324 which has been formed is subsequently removed from the front side 330. The $SiO_2$ 324 on the rear side 332 is structured, in order subsequently to be used as an etching mask 326.

Diamond 328 or DLC (diamond-like carbon) is deposited on the front side 330, for example with a thickness of about 1 μm. A chromium layer (not shown) is applied with a thickness of about 100 nm and structured. It is used as an etching mask for the structuring of the diamond 328, which is then carried out.

The diamond 328 is preferably structured by plasma etching, and the chromium mask is subsequently removed. FIG. 7 shows the particle filter after this step.

The front side 330 is now protected in an etching holder (not shown) and the silicon is wet-chemically etched anisotropically, starting from the rear side 332. For example, TMAH or potassium hydroxide may be envisaged as the etchant. The $SiO_2$ 324 on the rear side 332 is in this case used as an etching mask 326. After the end of the etching process, this layer is removed. The particle filter 214 is then in the form shown in FIG. 6. The membrane is therefore formed from diamond 328 in the exemplary embodiment according to FIGS. 5 to 9, while the carrier 314 is formed from the silicon 323 of the silicon wafer 322.

Figure 9:
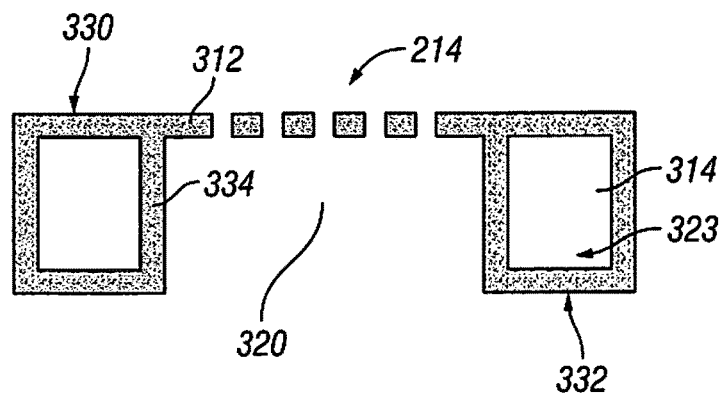
FIG. 9 a section as in FIG. 6 through a diamond-coated particle filter.

As represented in FIG. 9, the complete particle filter 214 may be coated with a diamond layer 334 in order to seal it, so as to provide an extremely stable particle filter 214 which is both chemically and mechanically resistant. Even the silicon 323 is protected, and the entire particle filter 214 is encapsulated with diamond 328. The only exception from this is any external surfaces which are exposed when sawing apart (separating) a plurality of particle filters 214 produced together on a multicomponent preform (silicon wafer 322).

The external surfaces, however, are generally separated anyway from the fluid to be filtered by sealing rings.

If such external surfaces are also intended to be protected, the individual chips or particle filters 214 may be coated with a diamond layer 334 after separating the wafer.

The additional diamond layer 334 reduces the diameter of the pores 316. This should already have been considered when structuring the chromium mask, in particular when a setpoint diameter of for example about 450 nm is intended to be obtained for the pores.

The particle filter 214 represented in FIG. 9 therefore receives a diamond layer 334 which protects it against chemical and mechanical effects.

As an alternative, the silicon 323 may be entirely removed so that individual thin filter membranes are obtained.

Using silicon with a (110) orientation has the advantage that vertical walls are created during the etching, so that a high packing density of particle filters 214 on a silicon wafer 322 is achieved. This may also be done by dry etching of the silicon, although this process is more expensive. In addition, in this case it is necessary to ensure that the etching process is ended when reaching the diamond 328.

The silicon wafer 322 may, however, also consist of silicon with a (100) orientation. Nevertheless, wet-chemical anisotropic etching of such a silicon wafer 322 produces oblique rather than perpendicular edges, so that the packing density is reduced.

Figure 8:
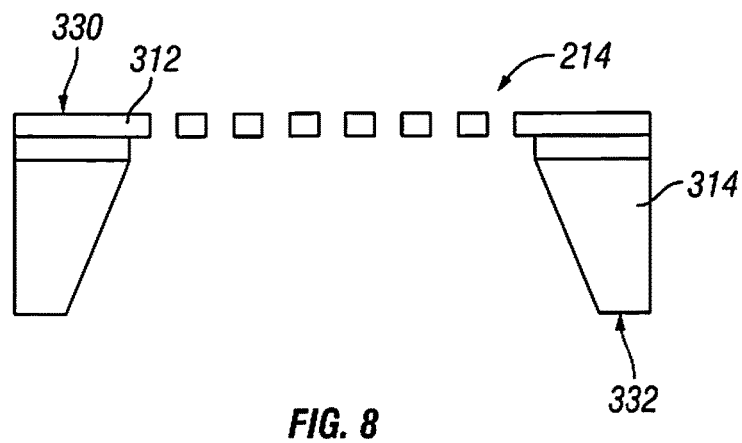
FIG. 8 is a section through another embodiment of the particle filter as in FIG. 6 with a different alignment of the lattice structure of a carrier.

As an alternative to thermally oxidized silicon ($SiO_2$ 324), it is also possible to use other etching masks, for example differently deposited $SiO_2$ 324 or $Si_3N_4$. It is likewise conceivable to employ SOI wafers or to use other methods. FIG. 8 shows a particle filter 214 when using SOI wafers with a (100) orientation.

The particle filters 214 manufactured by such an alternative process may subsequently be provided with a diamond layer 334, so as again to provide a particle filter 214 which is entirely protected by diamond 328. This method is more elaborate in terms of processing, but offers the advantage that the diamond layer 334 does not need to be structured.

Instead of silicon, other materials may also be used as a carrier 314 for the membrane 312 made of diamond 328.

In particular hard metal, titanium or refractory metals, such as for example W, Ta, Mo and carbides thereof, may be envisaged for this. SiC and $Si_3N_4$ are likewise particularly suitable.

The coating with diamond is carried out in particular by means of CVD (chemical vapor deposition) in a methane-hydrogen atmosphere. The energy required for dissociation of the gases is advantageously provided by a hot filament. Microwave plasma or arc-jet excitation are, however, also possible.

As described above, in order to detect the particles 222 they may be marked with fluorescent dyes. These dyes are excited by a laser and the emitted light is measured by the detector described in detail above.

Since diamond is transparent, using the particle filters 214 described here allows the illumination and the detection to be carried out from different sides.

The particle filters 214 with a membrane 312 made of diamond 328 are especially suitable, in particular, for the determination and measurement of viruses in media such as blood and saliva. To this end, finer pores 316 are used, for example with a diameter of 50 nm. Pores 316 with a very small diameter beyond the resolution limit of conventional exposure and structuring methods can be produced reproducibly if a completed particle filter, or one in which at least the diamond 328 is already structured, is coated with a further diamond layer 334. This narrows the pores 316.

In order to detect bacteria in drinking water, the hole diameter may be 450 nm. The membrane thickness is in this case approximately 1 µm.

The pores 316 should have a high verticality with respect to the surface of the membrane 12.

The roughness of the perforation on the inside of the pores 316 is rms<2 µm, preferably rms<100 nm and particularly preferably <50 nm.

The grain size of the diamond layer should be less than 1 µm, preferably less than 50 nm and particularly preferably less than 20 nm.

The flexural breaking stress of the diamond layer should be more than 1 GPa, preferably more than 4 GPa and particularly preferably more than 7 GPa. The Young's modulus should be more than 500 GPa, preferably more than 700 GPa and particularly preferably more than 1000 GPa.

The particle filter 214 allows bacteria enrichment in water or air by a micromechanical surface filter, for example in order to improve a detection limit of an analysis device. Owing to the use of diamond 328 in the membrane 312, the particle filter 214 has a high chemical and mechanical robustness. This means a high degree of reusability and therefore a high degree of automation.

As is described more specifically in DE 10 2006 026 559 A1, to which reference is explicitly made for further details, the particle filter may be used in a detection method in which the medium is pumped through a thin filter in order to detect certain particles in media (for example bacteria in drinking water). The particle filter 214 has pores 316 with a diameter adapted so that the particles to be detected, and all particles which are of the same size or larger, remain behind on the filter surface, i.e. are enriched there.

The high mechanical stability makes it possible to generate a high pressure difference between the two sides of the membranes, so that the flow rate through the filter can be increased. As an alternative or in addition, the pore density may be increased in order to increase the percentage of pore area in relation to the total area of the filter. This is beneficial particularly with a view to miniaturization of the overall system.

Both liquids and gases may be envisaged as media to be filtered. FIGS. 5 and 6 show a view of and a cross section through the particle filter used as a filter element. The pores are preferably round, although they may also have a different shape.

In order to permit fully automatic operation in a detection system, a fluidic system of the detection system and in particular the filter is cleaned after each studied sample. All previously supplied substances (sample to be studied, marking substances, auxiliary reagents, dirt and contaminants) are in this case removed by using aggressive chemicals, for example acids, alkalis or solvents for cleaning.

Such a fully automatic detection system will be explained in more detail below as a preferred use of the particle detection apparatus 210 with the aid of FIGS. 10 and 11.

Figure 10:
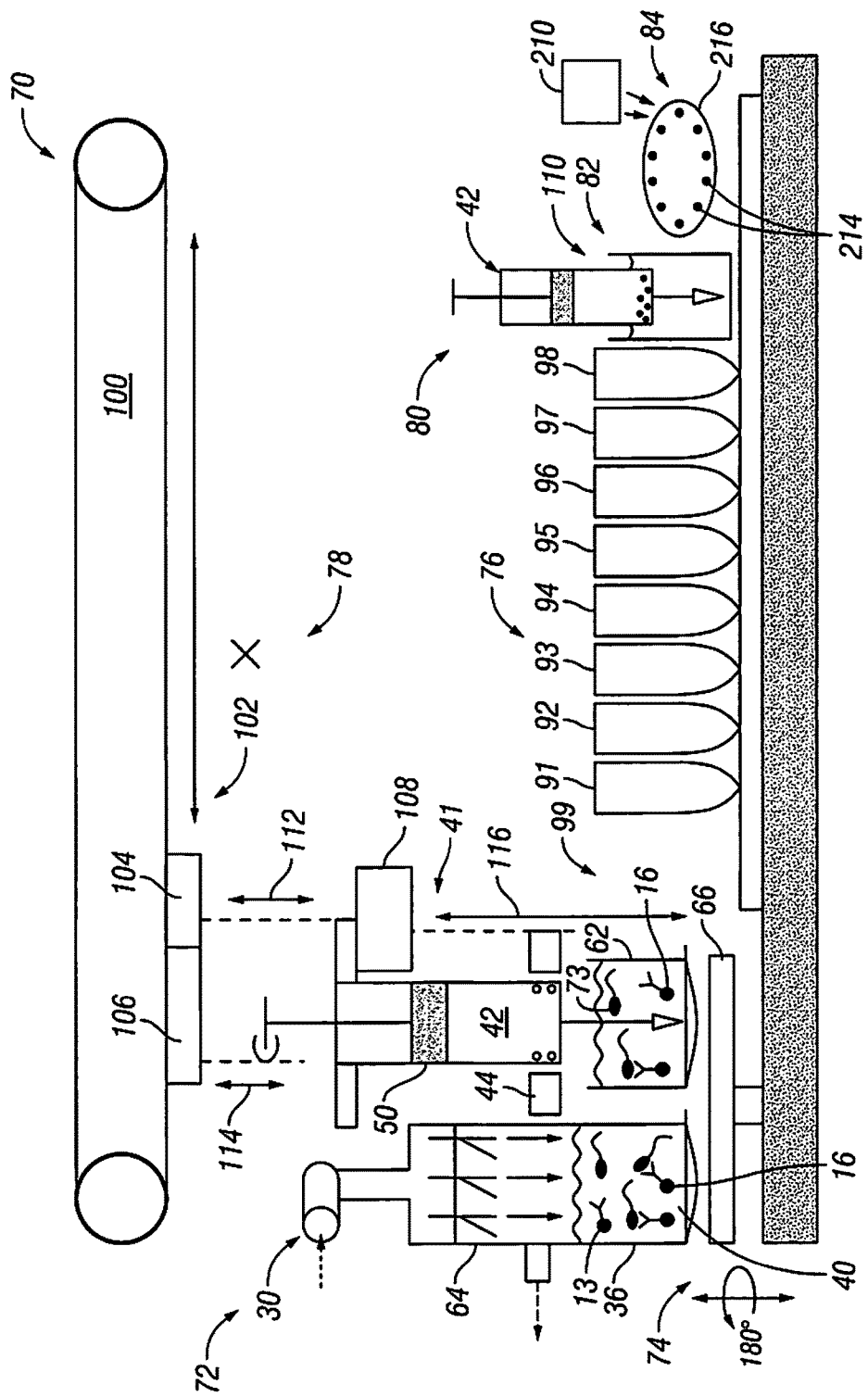
FIG. 10 is a side view of an overall system of a fully automatic apparatus for detecting particles.
Figure 11:
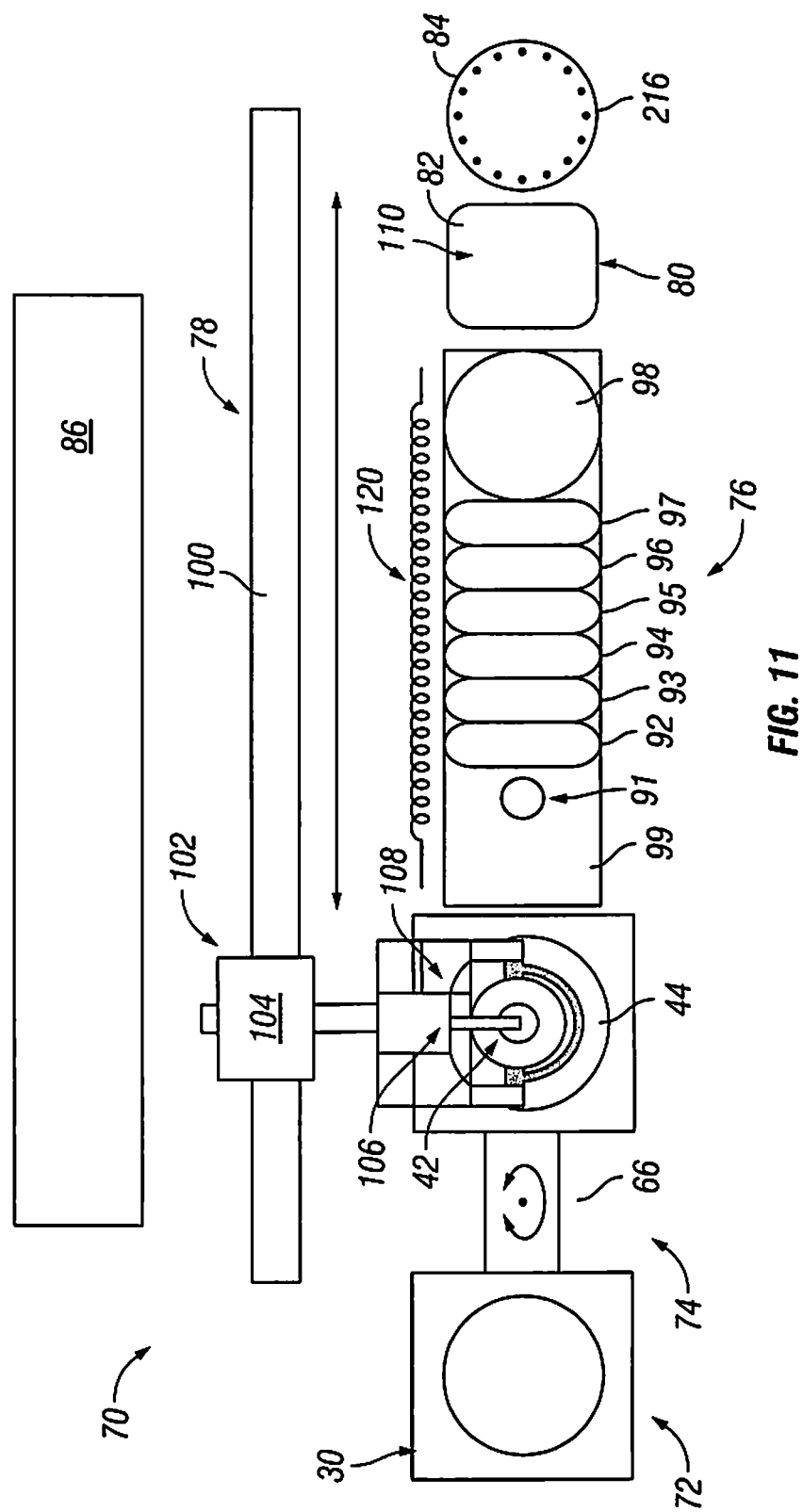
FIG. 11 is a plan view of the overall system.

The overall system represented in more detail in FIGS. 10 and 11 forms an (analysis) apparatus 70 for the automatic detection of in particular biological particles 222, 13 and has as its components a collection device 72, a transfer unit 74, a dosing unit 41, a magnet 44, a group 76 of reservoirs, a drive unit 78, a maceration device 80, optionally with a temperature regulation unit 82, a detection unit 84 and a control unit 86.

These possible components will be described in more detail below.

As the collection device 72, an air sampler 30 is preferably used, in particular an air sampler 30 from the company SKC (see U.S. Pat. No. 5,902,385 and U.S. Pat. No. 5,904,752) or the company Bertin. The air sampler 30 transfers particles 13, in particular microorganisms (bacteria, viruses) and toxins, from a gas phase into a collection liquid 40.

The transfer unit 74 preferably has a traveling/tilting unit 66. Since the preferred air sampler 30 is constructed in a modular fashion, and in particular consists of at least two components—nozzle fixture 64 and collection container 36, the nozzle fixture 64 can be removed and the collection container 36 transferred to the enrichment position. Here, for example, paramagnetic beads 16 for bonding with particles 13 to be detected may be received and enriched with the bonded particles. A further vessel 62 may optionally be used as an additional collection container.

The dosing unit 41 is preferably designed as a syringe 42. Using the dosing unit 41, for example, collection liquid 40 is taken up.

The magnet 44 is used as a separating device in order to concentrate the paramagnetic beads 16 in or on the dosing unit 41. When the magnet 44 is switched on or brought close, the beads 16 are magnetically fixed in the dosing unit even when it releases liquid. In this way, the beads 16 can be separated from the liquid surrounding them.

The group 76 has a plurality of reservoirs (vessels) 91-98 holding different liquids, which are needed for processing the particles 13. A resting position 99 is furthermore provided. In particular, the following liquid reservoirs are provided:

solution containing paramagnetic beads (first reservoir 91)
equilibration solution (second reservoir 92)
first maceration solution (third reservoir 93)
second maceration solution (fourth reservoir 94)
collection liquid, for example water (fifth reservoir 95)
cleaning solution (sixth reservoir 96)
preservative solution (seventh reservoir 97)
waste vessel (eighth reservoir 98)

The reservoirs 91-98 are preferably—together with the resting position 99 and the collection device 72—arranged in a line. In this way, the dosing unit 41 can be moved linearly by means of a simply constructed linear drive 100 between the reservoirs 91-98, optionally the resting position 99 and the collection device 72.

Furthermore, the overall system can then easily be expanded or reduced (according to the application purpose).

The drive unit 78 has the drives explained below in F) to I):

F) a linear drive 100 with a unit 102 for receiving the dosing unit 41 in order to move it to all the positions (preferably in only one dimension, here in the X direction);
G) a first movement unit (first motor 104) for moving the dosing unit 41 (preferably for moving the syringe 42) in the Z direction—first movement 112;
H) a second movement unit (second motor 106) for liquid dosing (preferably for moving a syringe piston 50)—second movement 114—and
I) a third movement unit (third motor 108) for bringing the magnet 44 closer or moving it further away (for example in the Z direction)—third movement 116.

The maceration device 80 preferably has an ultrasound instrument 56, particularly in the form of an ultrasound bath 110, for mechanical maceration of the particles, in particular microorganisms. The ultrasound bath 110 is filled with liquid, and the dosing unit 41 can dip into this liquid. In a second function, the ultrasound bath 110 at lower power may be used for resuspension of the paramagnetic beads 16.

In the example represented, the maceration device 86 furthermore has a temperature regulation unit 82, which may be operated together or separately with the ultrasound bath 110. The temperature regulation unit 82 is used to assist biochemical methods for maceration of the particles 13, in particular microorganisms (for example enzymatic digestion). Thermal maceration methods close to the boiling point are also possible with the temperature regulation unit.

For operation of the overall system at extreme temperatures, temperature regulation of the overall system is provided. In particular, the reagent reservoirs 91-97, the waste vessel 98 and the collection container 36 are thermally regulated by means of a second temperature regulation unit 119, indicated here by way of example as a heating coil.

The detection unit 84 is provided at the end of the process chain, and has the particle detection apparatus 210 with the particle filter 214. To this end, a rotatable disk is provided as a holding apparatus 216, in which a plurality of particle filters can be moved between a reception position for filtering out the particles 13, 222 and a detection position (represented in FIG. 1).

The control unit 86 indicated in FIG. 11 is used to control and monitor the overall system. For example, a computer or data-processing instrument is provided as the control unit 86, in which the individual control steps for fully automatic conduct of the detection method are stored in the form of control instructions as software.

At the same time, data transfer for example via the Internet (online) is possible by means of the control unit 86. The data transfer is used to compare the results by means of a database or to emit an alarm. Control of the overall system online is also possible, so that the system can be operated over sizeable distances.

At the end of a respective sampling carried out with the overall system above—apparatus 70—is the transfer of the beads 16 into or onto the detection unit 84.

To this end, the beads 16 are applied onto the membrane 312 of the particle filter 214, the surface 220 of which can then be used as a detection platform in the particle detection apparatus 210. To this end, in particular, the beads 16 are selected so that they have an extent greater than the size of the pores 316. In the particle detection apparatus 210, the aforementioned particle detection method for measuring the number of particles 13 is then carried out.

Use of non-paramagnetic beads 16 in the overall system may also be envisaged. Enrichment of the beads after the "air sampling" could be carried out instead by means of a magnetic field through a porous membrane, preferably a micromechanical filter.

To this end, in an embodiment of the apparatus 70 which is not represented in detail, the particle filter 214 is used as a separating device. Owing to the size of the pores 316, this particle filter 214 retains the beads 16 but lets liquids pass through. Consequently, all the washing and detection solutions which are required for analysis, detection of special particles or maceration, for example all the washing and detection solutions which are necessary for an immunodetection (ELISA), could be pumped through this micromechanical particle filter 214. To this end, it is very helpful for the chemical stability if the membrane 312 consists of diamond 328 or is coated therewith.

The particles 13, 222 correspondingly retained on the surface 220 of the particle filter 214, in particular by means of the beads 16, and optionally processed, are then counted by means of the particle detection apparatus 210.

All the features and method steps explained above with reference to individual embodiments may be combined with one another in any desired way; they may be present together in a particle detector apparatus 10 or a method, or individually in different versions.

What is claimed is:

1. A particle detector apparatus for optically ascertaining a number of particles arranged on a surface, the particle detector apparatus comprising:
a mobile light source configured to emit source light onto the surface, the surface being on a particle filter that includes a membrane that defines a plurality of pores configured to filter the particles from a medium, and at least one subregion of a surface of the membrane which is accessible for the medium includes transparent carbon material having a diamond structure;
a spatially resolving light detector;
an optical focusing device configured to focus image light that is emitted from the surface in response to the source light onto the spatially resolving light detector, the spatially resolving light detector including light sensors that are configured to measure brightness values based on the image light, such that the spatially resolving light detector is configured to produce image data based on the brightness values delivered by the light sensors; and
an evaluation device configured to ascertain the number of particles based on the image data.

2. The particle detector apparatus as claimed in claim 1, wherein
the light sensors include at least one of the following: an integrated circuit, a charged coupled device (CCD), a complementary metal oxide semiconductor (CMOS) and a diode array.

3. The particle detector apparatus as claimed in claim 1, wherein
the light source includes a light emitting device.

4. The particle detector apparatus as claimed in claim 1, wherein
the light source includes a LASER.

5. The particle detector apparatus as claimed in claim 1, wherein
at least one of the light source and the focusing device includes an optical filter.

6. The particle detector apparatus as claimed in claim 5, further comprising
a filter changing device configured to change the optical filter.

7. The particle detector apparatus as claimed in claim 1, wherein
the light sensors are arranged in a grid;
the particle detector apparatus further includes a beam splitter that is configured to distribute an image of the surface onto the light sensors which are configured to produce the image data; and
the evaluation device is configured to compile an overall image from the image data provided by the light sensors.

8. The particle detector apparatus as claimed in claim 1, further comprising
a positioning device on which at least one of the light sensors is disposed for positioning relative to the surface.

9. The particle detector apparatus as claimed in claim 1, wherein
the light sensors include a CCD row; and
the particle detector apparatus further includes a deflection device that is configured to project different sections of an image of the surface onto the CCD row.

10. The particle detector apparatus as claimed in claim 1, further comprising:
a collecting device configured to contain a collecting fluid including separating particles that are selectively bound to the particles provided from a particle-fluid mixture;
a separating device configured to separate from the collecting fluid those of the separating particles that are bound to particles; and
a detecting device that includes the evaluation device and is configured to detect an amount of the particles based on the separating particles that are separated from the collecting fluid by the separating device.

11. The apparatus as claimed in claim 10, further comprising
a dosing unit configured to contain the collecting fluid and further configured to fill the collecting device with the collecting fluid.

12. The apparatus as claimed in claim 11, wherein
the dosing unit includes a separating device that is configured to selectively retain certain of the separating particles and dispense other of the separating particles with the collecting fluid into the collecting device.

13. The apparatus as claimed in claim 11, wherein
the dosing unit includes a syringe or a pipette.

14. The apparatus as claimed in claim 11, wherein
the dosing unit is configured for movement by a drive unit that is positioned between the collecting device and the detection unit.

15. The apparatus as claimed in claim 11, further comprising
a drive unit configured to selectively move the dosing unit to different reservoirs to receive the collecting fluid.

16. The apparatus as claimed in claim 11, wherein
the separating device includes a micromechanical filter defining pores having diameters that are greater than a diameter of the particles and less than a diameter of the separating particles.

17. The apparatus as claimed in claim 11, wherein
the collecting device includes a gas collection device configured to convey the particles from a gas containing the particles into the collecting fluid that contains the separating particles.

18. The apparatus as claimed in claim 11, wherein
the collecting device includes a separate collection container that is configured to contain the collecting fluid and configured for movement by a transfer unit between a collection position in which a particle-fluid mixture is guided through the collecting fluid and a position at which the collecting container contains the collecting fluid.

19. The apparatus as claimed in claim 18, wherein
the transfer unit is configured for raising, lowering and tilting the collecting container.

20. The apparatus as claimed in claim 1, further comprising
a plurality of reservoirs configured to provide different fluids for use by the detecting device during detection of the particles.

21. The apparatus as claimed in claim 20,
wherein the reservoirs are configured to contain at least one of the following:
separating particle body solution,
equilibration solution,
maceration solution, the collecting fluid,
cleaning solution, and
preservation solution.

22. The apparatus as claimed in claim 20, further comprising
a waste vessel associated with the plurality of reservoirs.

23. The apparatus as claimed in claim 1, further comprising
at least one controllable motor configured to drive a dosing unit for dosed reception and delivery of liquids containing the particles.

24. A particle detector apparatus for optically ascertaining a number of particles arranged on a surface, the particle detector apparatus comprising:
a collecting device configured to contain a collecting fluid including separating particles that are selectively bound to the particles provided from a particle-fluid mixture;
a dosing unit configured to contain the collecting fluid and further configured to fill the collecting device with the collecting fluid;
a separating device configured to separate from the collecting fluid those of the separating particles that are bound to particles, the separating device including a magnet that is configured to magnetically interact with the separating particles;
a light source configured to emit source light onto the surface, the surface being on a particle filter that includes a membrane that defines a plurality of pores configured to filter the particles from a medium, and at least one subregion of a surface of the membrane which is accessible for the medium includes transparent carbon material having a diamond structure;
a spatially resolving light detector;
an optical focusing device configured to focus image light that is emitted from the surface in response to the source light onto the spatially resolving light detector, the spatially resolving light detector including light sensors that are configured to measure brightness values based on the image light, such that the spatially resolving light detector is configured to produce image data based on the brightness values delivered by the light sensors; and
a detecting device that includes an evaluation device configured to ascertain the number of particles based on the image data, the detecting device being configured to detect the number of the particles based on the separating particles that are separated from the collecting fluid by the separating device.

25. The apparatus as claimed in claim 24, wherein
the magnet is disposed on at least one of a wall of a dosing chamber of a dosing unit that is configured to provide the collecting fluid to the collecting device and a piston bottom of a piston of the dosing unit.

26. The apparatus as claimed in claim 24, wherein
the magnet includes a permanent magnet that is moveable to a first position for retaining the separating particles and to a second position for releasing the separating particles.

* * * * *